US 8,801,665 B2

(12) United States Patent
Sabbah

(10) Patent No.: US 8,801,665 B2
(45) Date of Patent: Aug. 12, 2014

(54) APPARATUS AND METHOD FOR CONTROLLED DEPTH OF INJECTION INTO MYOCARDIAL TISSUE

(75) Inventor: Hani N. Sabbah, Waterford, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 12/421,541

(22) Filed: Apr. 9, 2009

(65) Prior Publication Data

US 2009/0259212 A1    Oct. 15, 2009

Related U.S. Application Data

(60) Provisional application No. 61/123,661, filed on Apr. 10, 2008.

(51) Int. Cl.
*A61M 5/00* (2006.01)

(52) U.S. Cl.
USPC .......................... 604/117; 604/511; 604/115

(58) Field of Classification Search
USPC ............... 604/507, 510, 506, 115, 117, 511
See application file for complete search history.

(56) References Cited

U.S. PATENT DOCUMENTS

| | | | |
|---|---|---|---|
| 5,002,067 A | 3/1991 | Berthelsen et al. | |
| 5,324,325 A | 6/1994 | Moaddeb | |
| 5,419,777 A | 5/1995 | Hofling et al. | |
| 5,431,649 A | 7/1995 | Mulier et al. | |
| 5,447,533 A | 9/1995 | Vachon et al. | |
| 5,531,780 A | 7/1996 | Vachon | |
| 5,551,427 A | 9/1996 | Altman | |
| 6,063,061 A | 5/2000 | Wallace et al. | |
| 6,086,565 A | 7/2000 | Ouchi | |
| 6,132,451 A | 10/2000 | Payne et al. | |
| 6,238,406 B1 | 5/2001 | Ellis et al. | |
| 6,360,749 B1 | 3/2002 | Jayaraman | |

(Continued)

FOREIGN PATENT DOCUMENTS

| | | |
|---|---|---|
| JP | 60-160808 | 10/1985 |
| JP | 64-022360 | 2/1989 |

(Continued)

OTHER PUBLICATIONS

ISA/EPO, International Search Report for App No. PCT/US2009/002269 filed Apr. 10, 2009, Jun. 4, 2009, 6 pages.

(Continued)

*Primary Examiner* — Quynh-Nhu H Vu
*Assistant Examiner* — Brandy S Lee
(74) *Attorney, Agent, or Firm* — David H. Carroll

(57) ABSTRACT

An injector for delivering an injectate into the myocardium of the heart may be implemented as a catheter or a handheld unit. The injector includes a body, a stabilizer secured to a distal end of the body, and a needle that may be controllably advanced from the distal end of the body. The stabilizer stabilizes the distal end of the body relative to the myocardium while the heart beats. An enlarged region disposed along the needle prevents the needle from being advanced into the myocardium beyond a desired penetration depth. To make an injection, the physician brings the distal end of the body in proximity to the myocardium, actuates the stabilizer to stabilize the distal end relative to the myocardium, and advances the needle into the myocardium. Advancement of the needle is impeded by the enlarged region, thereby placing the needle tip at the desired penetration depth for the injection.

16 Claims, 5 Drawing Sheets

(56) References Cited

U.S. PATENT DOCUMENTS

| | | | |
|---|---|---|---|
| 6,416,510 | B1 | 7/2002 | Altman et al. |
| 6,447,443 | B1 | 9/2002 | Keogh et al. |
| 6,493,591 | B1 | 12/2002 | Stokes |
| 6,508,824 | B1 | 1/2003 | Flaherty et al. |
| 6,585,716 | B2 | 7/2003 | Altman |
| 6,689,103 | B1 | 2/2004 | Palasis |
| 6,702,777 | B2 | 3/2004 | Haim et al. |
| 7,031,775 | B2 | 4/2006 | Soykan et al. |
| 7,044,905 | B2 | 5/2006 | Vidlund et al. |
| 7,094,230 | B2 | 8/2006 | Flaherty et al. |
| 7,103,418 | B2 * | 9/2006 | Laske et al. ............. 607/120 |
| 7,104,988 | B2 | 9/2006 | Altman et al. |
| 7,186,210 | B2 | 3/2007 | Feld et al. |
| 7,189,199 | B2 | 3/2007 | McCarthy et al. |
| 2002/0077687 | A1 | 6/2002 | Ahn |
| 2002/0082469 | A1 | 6/2002 | Taheri |
| 2002/0169360 | A1 | 11/2002 | Taylor et al. |
| 2002/0177772 | A1 * | 11/2002 | Altman et al. ............. 600/431 |
| 2002/0188170 | A1 | 12/2002 | Santamore et al. |
| 2003/0078671 | A1 | 4/2003 | Lesniak et al. |
| 2004/0005295 | A1 | 1/2004 | Lee et al. |
| 2004/0010231 | A1 * | 1/2004 | Leonhardt et al. ....... 604/170.03 |
| 2004/0023842 | A1 | 2/2004 | Pathak et al. |
| 2004/0030286 | A1 | 2/2004 | Altman |
| 2004/0102759 | A1 | 5/2004 | Altman et al. |
| 2004/0208845 | A1 | 10/2004 | Michal et al. |
| 2005/0003010 | A1 | 1/2005 | Cohen et al. |
| 2005/0080402 | A1 | 4/2005 | Santamore et al. |
| 2005/0271631 | A1 | 12/2005 | Lee et al. |
| 2006/0041243 | A1 | 2/2006 | Nayak et al. |
| 2006/0083717 | A1 | 4/2006 | Lee et al. |
| 2006/0083721 | A1 | 4/2006 | Cohen et al. |
| 2006/0149123 | A1 | 7/2006 | Vidlund et al. |
| 2007/0014784 | A1 | 1/2007 | Nayak et al. |
| 2007/0038052 | A1 | 2/2007 | Swoyer et al. |
| 2007/0042016 | A1 | 2/2007 | Nayak et al. |
| 2007/0093748 | A1 | 4/2007 | Nayak et al. |
| 2007/0172472 | A1 | 7/2007 | Nayak |
| 2007/0239134 | A1 | 10/2007 | Lesh et al. |
| 2008/0065048 | A1 | 3/2008 | Sabbah et al. |
| 2008/0069801 | A1 | 3/2008 | Lee et al. |

FOREIGN PATENT DOCUMENTS

| | | |
|---|---|---|
| JP | 11-114058 | 4/1999 |
| JP | 2000-037456 | 2/2000 |
| JP | 2001-516612 | 10/2001 |
| JP | 2003-529409 | 10/2003 |
| JP | 2004-533294 | 11/2004 |
| JP | 2004-533294 A | 11/2004 |
| JP | 2008-509754 | 4/2008 |
| WO | 9913785 A1 | 3/1999 |
| WO | 0110313 A1 | 2/2001 |
| WO | 0126706 A2 | 4/2001 |
| WO | WO 02/24248 A1 | 3/2002 |
| WO | 02087481 A1 | 11/2002 |
| WO | 03043507 A2 | 5/2003 |
| WO | 03094855 A1 | 11/2003 |
| WO | 03095016 A1 | 11/2003 |
| WO | 2004050013 A2 | 6/2004 |
| WO | 2004091592 A2 | 10/2004 |
| WO | 2005102181 A1 | 11/2005 |
| WO | 2006020943 A1 | 2/2006 |
| WO | 2007024414 A2 | 3/2007 |
| WO | 2009119787 A1 | 10/2009 |
| WO | 2009126323 A1 | 10/2009 |

OTHER PUBLICATIONS

ISA/EPO, Written Opinion for App. No. PCT/US2009/002269 filed Apr. 4, 2009, Jun. 4, 2009, 6 pages.

U.S. Appl. No. 61/123,661, filed Apr. 10, 2008, Sabbah (not published).

Bioheart, Inc., Bioheart News, vol. 1, No. 2, 2000, 8 pages.

Henry Ford Health System, Voluntary Amendment, European Patent Application No. 09 730 816.7, Jan. 10, 2011, 7 pages.

Christman, Karen L. et al., Injectable Fibrin Scaffold Improves Cell Transplant Survival, Reduces Infarct Expansion, and Induces Neovasculature Formation in Ischemic Myocardium, J. American Col. of Cardiology, vol. 44, No. 3, Aug. 4, 2004, pp. 654-660.

Christman, Karen L. et al., Fibrin Glue Alone and Skeletal Myoblasts in a Fibrin Scaffold Preserve Cardiac Function After Myocardial Infarction, Tissue Engineering, vol. 10, No. 3/4, 2004, pp. 403-409.

Henry Ford Health System, Article 19 Amendment, International Patent Application No. PCT/US2009/002269, Jul. 31, 2009, 3 pages.

Huang, Ngan F. et al., Injectable Biopolymers Enhance Angiogenesis After Myocardial Infarction, Tissue Engineering, vol. 11, No. 11/12, 2005, pp. 1860-1866.

Kofidis, Theo et al., Injectable Bioartificial Myocardial Tissue for Large-Scale Intramural Cell Transfer and Functional Recovery of Injured Heart Muscle, J. Thoracic Cardiovascular Surg., vol. 128, No. 4, Oct. 2004, pp. 571-578.

Landa, Natali, et al., Effect of Injectable Alginate Implant on Cardiac Remodeling and Function After Recent and Old Infarcts in Rat, Circulation, vol. 117, Mar. 2008, pp. 1388-1396.

Rastogi, Sharad, et al., Reversal of Maladaptive Gene Program in Left Ventricular Myocardium of Dogs With Heart Failure Following Long-Term Therapy with the Acorn Cardiac Support Device, Heart Failure Reviews, vol. 10, 2005, pp. 157-163.

Sabbah, Hani N., The Cardiac Support Device and the Myosplint: Treating Heart Failure by Targeting Left Ventricular Size and Shape, Ann. Thorac Surg., vol. 75, 2003, S13-S19.

Sabbah, Hani N., Global Left Ventricular Remodeling With the Acorn Cardiac Support Device: Hemodynamic and Angiographic Findings in Dogs With Heart Failure, Heart Failure Rev., vol. 10, 2005, pp. 109-115.

Sabbah et al., Reversal of Chronic Molecular and Cellular Abnormalities Due to Heart Failure by Passive Mechanical Ventrical Containment, Circulation Research, vol. 93, Nov. 28, 2003, pp. 1095-1101.

Japanese Patent Office, Office Action: Japanese Patent Application No. 2009-524718, Mar. 28, 2012, 3 pages.

Japanese Patent Office, Office Action: Japanese Patent Application No. 2009-527418, Mar. 28, 2012, 3 pages.

Japanese Patent Office, Office Action (Translation): Japanese Patent Application No. 2009-527418, Mar. 28, 2012, 4 pages.

Japanese Patent Office. Final Office Action: Japanese Patent Application No. 2011-504014, Feb. 26, 2014. 4 Pages.

Australian Patent Office. Office Action: Australian Patent Application No. 2009234321, Jul. 25, 2013. 3 pages.

Australian Patent Office. Office Action: Australian Patent Application No. 2009234321, Aug. 21, 2013. 3 pages.

Henry Ford Health System. Reply to Office Action (Written Argument): Japanese Patent Application No. 2011-504014, Nov. 19, 2013. 22 Pages.

Japanese Patent Office. Office Action: Japanese Patent Application No. 2011-504014, Jul. 19, 2013. 5 pages.

* cited by examiner

APPARATUS AND METHOD FOR CONTROLLED DEPTH OF INJECTION INTO MYOCARDIAL TISSUE

CROSS-REFERENCE TO RELATED APPLICATIONS

This application claims the benefit of U.S. Provisional Patent Application Ser. No. 61/123,661, filed Apr. 10, 2008, which hereby is incorporated herein in its entirety by reference thereto.

BACKGROUND OF THE INVENTION

1. Field of the Invention

The present invention relates to the treatment of cardiac conditions, and more particularly, to apparatus and methods for controlling depth of injection into myocardial tissue.

2. Description of Related Art

Heart failure ("HF") is generally defined as a change in the pumping function of the heart accompanied by typical signs or symptoms. Heart failure is a progressive disorder whereby the hemodynamic and symptomatic states of the patient worsen over time despite the absence of clinically apparent adverse events. The symptomatic deterioration is often accompanied by progressive left ventricular ("LV") chamber remodeling.

Preventing or reversing remodeling has emerged as desirable in the treatment of cardiomyopathy. Cardiomyopathy is a general term for disease of heart muscle regardless of the underlying etiology, which may be, for example, ischemic, hypertensive, dilated, hypertrophic, infiltrative, restrictive, viral, postpartum, valvular, or idiopathic. Cardomyopathy typically results in heart failure.

Myocardial infarction ("MI") is a medical emergency in which some of the heart's blood supply is suddenly and severely reduced or cut off, causing the myocardium to die because it is deprived of its oxygen supply. A myocardial infarction may progressively advance into heart failure. Scar tissue formation and aneurysmal thinning of the infarct region often occur in patients who survive myocardial infarctions. It is believed that the death of cardiomyocytes results in negative left ventricular (LV) remodeling which leads to increased wall stress in the remaining viable myocardium. This process results in a sequence of molecular, cellular, and physiological responses which lead to LV dilation. Negative LV remodeling is generally considered an independent contributor to the progression of heart failure.

Mitral regurgitation ("MR") is incompetency of the mitral valve causing flow from the left ventricle (LV) into the left atrium during systole. Common causes include mitral valve prolapse, ischemic papillary muscle dysfunction, rheumatic fever, and annular dilation secondary to LV systolic dysfunction and dilation. MR may lead to heart failure.

At the present time, the most effective treatment for patients in end-stage heart failure is heart transplantation. However, given the chronic shortage of donor hearts, alternate strategies are needed to improve the lives of those with heart failure. Moreover, transplantation is not the most suitable treatment option for patients with milder forms of the disease. Other treatment approaches include the delivery of drugs to the site of action through the bloodstream, and the injection of cells into ischemic myocardium to improve cardiac function. An example of an approach for treating cardiovascular problems with an intramyocardial scaffold is disclosed in United States Patent Application Publication No. 2005/0271631, published Dec. 8, 2005 in the name of Lee et al. and entitled "Material compositions and related systems and methods for treating cardiac conditions."

One of the approaches described in the Lee Published Patent Application uses a needle to inject the material that forms the intramyocardial scaffold into the myocardium. Care should be taken to ensure that the needle use for the injection is placed at an appropriate depth in the myocardium.

SUMMARY OF THE INVENTION

Despite care taken by a physician, it is possible that a needle used for an intramyocardial injection may penetrate too shallowly or too deeply into the myocardium, or even puncture the myocardium. This and other disadvantages of prior injection techniques are overcome by the present invention. Additional improvements and advantages may be recognized by those of ordinary skill in the art upon study of this disclosure.

One embodiment of the invention is an apparatus for administering an injectate into myocardial tissue of a heart of a patient, comprising a body having a distal portion; a stabilizer disposed at the body distal portion for stabilizing the body distal portion relative to the myocardial tissue; a needle; and a lumen disposed in the body for receiving the injectate. The needle, which is controllably extendable distally from the body distal portion, comprises a needle tip and an enlarged region disposed along the needle a predetermined distance from the needle tip for limiting penetration of the needle into the myocardial tissue to a predetermined penetration depth during distal extension. The needle further comprises an injection port distal of the enlarged region, the lumen being in fluid communication with the injection port through the needle.

Another embodiment of the invention is a method for administering an injectate into myocardial tissue of a heart in a body of a patient, comprising advancing a distal portion of a body into proximity with the myocardial tissue; stabilizing the body distal portion relative to the myocardial tissue; advancing a needle from the stabilized body distal portion into the myocardial tissue until impeded by an enlarged region disposed along the needle at a predetermined distance from a tip thereof; and administering the injectate into the myocardial tissue from an injection port in the needle distal of the enlarged region. The injectate penetrates into the myocardial tissue at a predetermined distance from an epicardial or endocardial surface of the heart.

Another embodiment of the present invention is a method for administering an injectate into myocardial tissue of a heart in a body of a patient, comprising advancing a distal end of a catheter body through a thoracic cavity into proximity with an epicardial surface of the myocardial tissue; stabilizing the distal end of the catheter body relative to the myocardial tissue; advancing a needle from the stabilized distal end of the catheter body into the myocardial tissue until impeded at the epicardial surface by an enlarged region disposed along the needle at a predetermined distance from a tip thereof, to achieve a predetermined penetration depth; and administering the injectate into the myocardial tissue from the tip of the needle. The injectate penetrates into the myocardial tissue at the penetration depth.

Other features and advantages of the inventions will become apparent from the following detailed description and from the claims.

Figure 1:
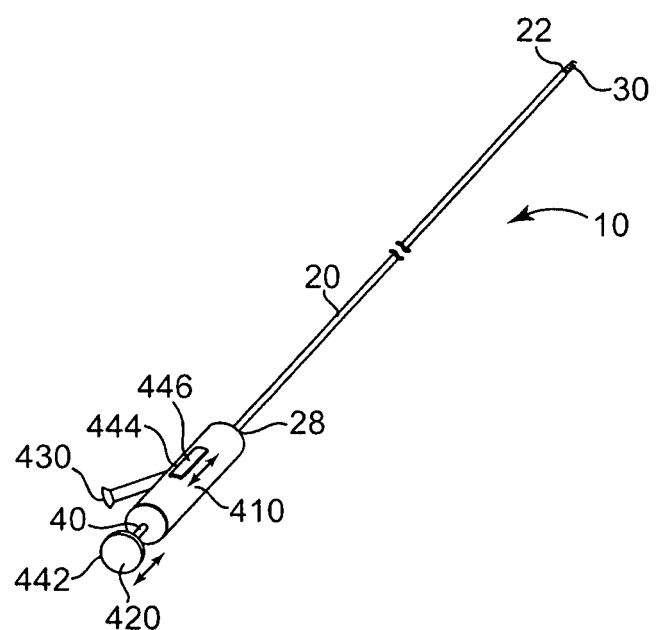
FIG. 1 is a perspective view of an exemplary implementation of an injector apparatus.

The Figures are to facilitate explanation of the present invention. The number, position, relationship and dimensions of the parts shown in the Figures to form the various implementations described herein, as well as dimensions and dimensional proportions to conform to specific force, weight, strength, flow and similar requirements, are explained herein or are understandable to a person of ordinary skill in the art upon study of this disclosure. Where used in various Figures, the same numerals designate the same or similar parts. Furthermore, when the terms "top," "bottom," "right," "left," "forward," "rear," "first," "second," "inside," "outside," and similar terms are used, the terms should be understood in reference to the orientation of the structures shown in the drawings and utilized to facilitate understanding. Similarly, when the terms "proximal," "distal," and similar positional terms are used, the terms should be understood in reference to the structures shown in the drawings and utilized to facilitate understanding.

DETAILED DESCRIPTION OF THE INVENTION, INCLUDING THE BEST MODE

An injector apparatus and associated methods for safely and repeatedly delivering an injectate at a predefined depth into the myocardium of the heart are described herein. The injector may be catheter-based or implemented in a handheld unit for use in open chest procedures. The catheter-based injector apparatus includes a catheter body, a stabilizer secured to a distal end of the catheter body for stabilizing the distal end of the catheter relative to the myocardium, and a needle that may be controllably advanced from the distal end of the catheter body into the myocardium. The stabilizer employs any suitable technique for stabilizing the distal end of the catheter body relative to the myocardium while the heart is in motion from systolic and diastolic cardiac movements. An enlarged region of the needle functions as a stop to prevent the needle from being advanced into the myocardium beyond a desired penetration depth. To make an injection, the physician advances the distal end of the catheter in proximity to the endocardium or the epicardium using any suitable technique, actuates the stabilizer to stabilize the distal end relative to the myocardium; and advances the needle into the myocardium. Advancement of the needle into the myocardium is impeded by the enlarged region, thereby placing the needle tip at the desired penetration depth and avoiding puncturing of the heart. The injection is then made, illustratively through one or more injection ports at the needle tip and/or in the sidewall of the needle distal of the enlarged region. After the injection is completed, the needle and catheter are removed.

The injector apparatus is suitable for any injectate that can pass through one or more lumen. Examples of suitable injectates include biologically compatible single or multiple component polymers, polymer-based beads, and polymer hydrogels, which may be injected to provide a therapeutic wall support or tissue engineering scaffold within the heart, or to induce angiogenesis, or to recruit cells, or to prevent apoptosis to expedite myocardial repair or reconstruction. Suitable polymers include fibrin glue, collagen, alginates, polyethylene glycol ("PEG"), and chitosan. The polymers may consist of only polymer material, or may include cells such as stem cells, fibroblasts, or skeletal cells; proteins, plasmids, or genes; growth factors in either protein or plasmid form; chemo-attractants; fibrin factor (or fragment) E; RDG binding sites; various pharmaceutical compositions; neo-tissues; or other therapeutically beneficial materials; or any combination of the foregoing.

Depending on the therapeutic effect sought, the injection may be to a single location in the myocardium, or to multiple sites in a pattern. Patterned multiple site injection is described in US Patent Application Publication No. 2008/0065048 published Mar. 13, 2008 (Sabbah et al., Intramyocardial Patterning for Global Cardiac Resizing and Reshaping), which hereby is incorporated herein in its entirety by reference thereto.

The Figures referenced herein generally illustrate various exemplary implementations of the injector apparatus and injection methods. These illustrated implementations are not meant to limit the scope of coverage, but rather to assist in understanding the context of the language used in this specification and in the claims. Accordingly, variations of the injector apparatus and injection methods that differ from the illustrated implementations may be encompassed by the appended claims, which alone define the invention.

FIG. 1 illustrates by broken perspective view an implementation of a catheter-based injector apparatus 10. The injector apparatus 10 includes a catheter body 20 secured to a handle 410. The catheter body 20 defines a catheter body distal end 22 and a catheter body proximal end 28, and the catheter body proximal end 28 is secured to the handle 410. The catheter body distal end 22 includes a fixation structure 30. For purposes of illustration, the fixation structure 30 is shown as extending forth from the catheter body distal end 22, although the fixation structure 30 may be withdrawn into the catheter body 20 as the catheter body distal end 22 is navigated to the injection site 500. Preferably, the catheter body distal end 22 is atraumatic in order to be navigable through various bodily passages to an injection site 500 (FIG. 2C).

Figure 2A:
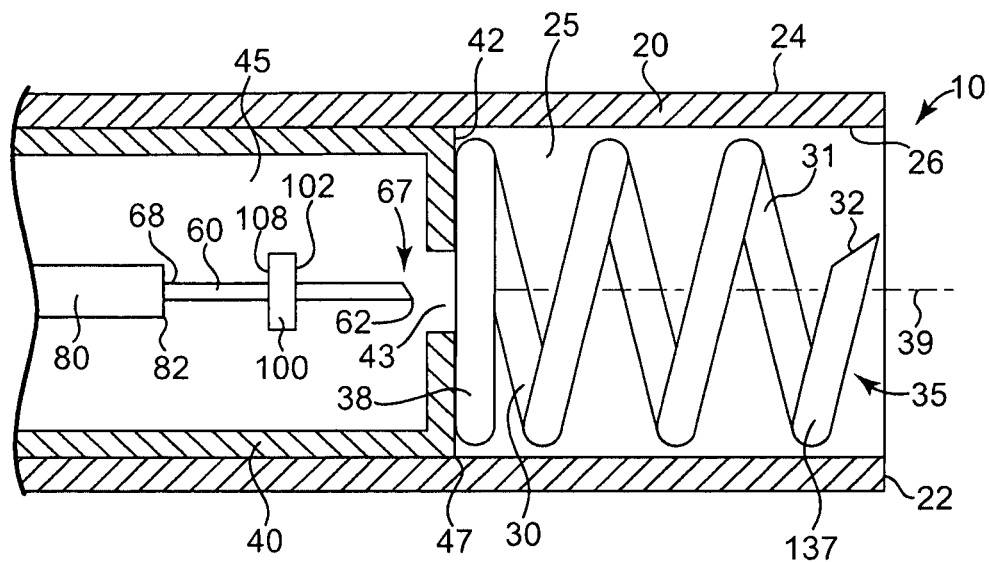
FIG. 2A is a partial cross-section view of a distal portion of an exemplary implementation of the injector apparatus of FIG. 1 in a first operational position.
Figure 2B:
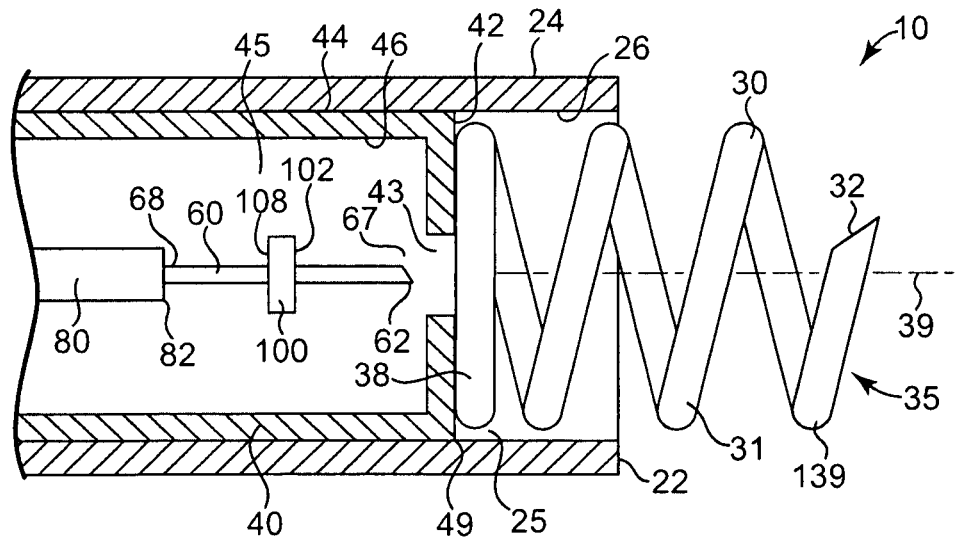
FIG. 2B is a partial cross-section view of a distal portion of an exemplary implementation of the injector apparatus of FIG. 1 in a second operational position.
Figure 2C:
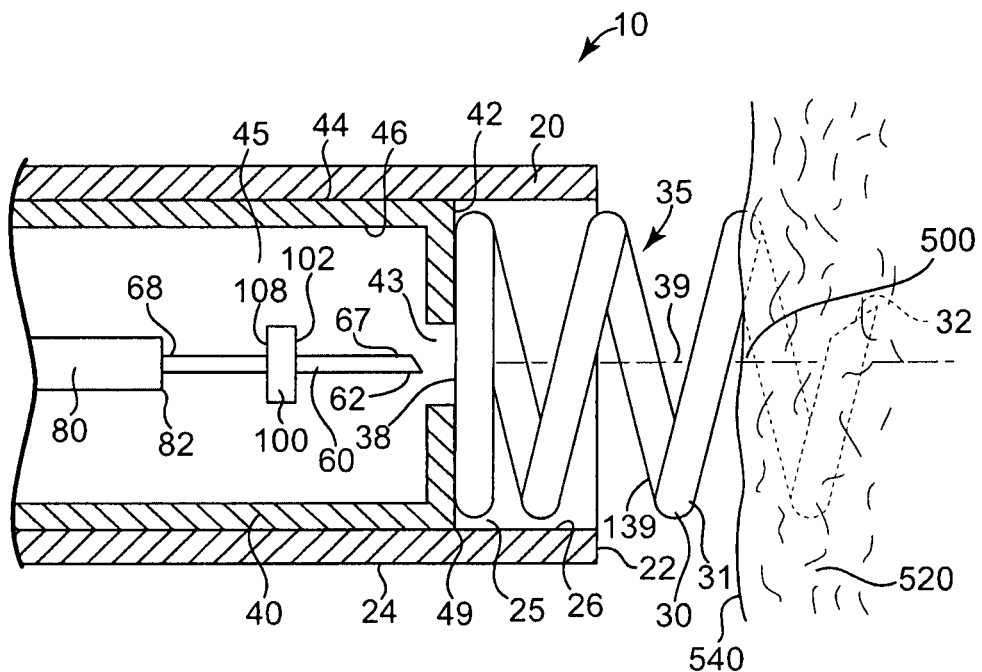
FIG. 2C is a partial cross-section view of a distal portion of an exemplary implementation of the injector apparatus of FIG. 1 in a in a third operational position.

As further shown in FIG. 2C, the fixation structure 30 may include portions configured as a helix designed to be affixed to tissue 520 generally proximate the injection site 500 by being screwed into the tissue 520 (FIG. 2).

In the illustrative implementation of FIG. 1, the catheter body proximal end 28 is secured to handle 410, which allows the physician to manipulate the catheter body 20 in order to direct the catheter body distal end 22 to the injection site 500. As illustrated, a drive shaft 40 may engage a driver knob 420, which is rotatably secured to the handle 410. The drive shaft 40 cooperates with the fixation structure 30 and with the driver knob 420 to allow the physician to screw the fixation structure 30 into the tissue 520 by rotation of the driver knob 420 to a fixation depth 180. Accordingly, various gears and other mechanical features as would be recognized by those of ordinary skill in the art upon study of this disclosure may be provided about the handle 410 and/or about the catheter body 20 so that the fixation structure 30 may cooperate with the driver knob 420 via the drive shaft 40.

One or more ports 430 may be placed about the handle 410 and/or the catheter body 20 generally proximate the catheter body proximal end 28. The ports 430 communicate with various lumens within the catheter body 20 to allow, for example, for the introduction/withdrawal of guidewire(s) and/or introduction of injectate.

FIGS. 2A to 2E show portions of the illustrative injector apparatus 10 at the catheter body distal end 22 in various operational conditions. As illustrated in FIG. 2A, the catheter body 20 defines a catheter body outer wall 24 and a catheter body inner wall 26, and a catheter body lumen 25 is defined by the catheter body inner wall 26. As illustrated, the drive shaft 40 defines a drive shaft outer wall 44 and a drive shaft inner wall 46, and a drive shaft lumen 45 is defined by the drive shaft inner wall 46. The drive shaft 40 is rotatably received within the catheter body lumen 25 to allow the physician to screw the fixation structure 30 into tissue 520 generally proximate the injection site 500. Portions of the drive shaft 40 may be biased against the catheter body inner wall 26, support structures may be placed along the length of the catheter body lumen 25 to support rotatably the drive shaft 40 within the catheter body lumen 25, and/or the drive shaft 40 may be otherwise mounted within the catheter body lumen 25 to be rotatable in ways readily recognizable by those of ordinary skill in the art upon study of this disclosure.

A fixation structure proximal end 38 of the fixation structure 30 is secured to the drive shaft distal end 42 of the drive shaft 40. The drive shaft distal end 42 is positioned between at least a drive shaft first position 47 (FIG. 2A) and a drive shaft second position 49 (FIG. 2B) in order to position the fixation structure 30 between at least a first fixation structure position 137 and a second fixation structure position 139. In the drive shaft first position 47, as illustrated in FIG. 2A, the fixation structure 30 is in the first fixation structure position 137 wherein the fixation structure 30 is contained within the outer body lumen 25 generally proximate the catheter body distal end 22 in order to allow the catheter body distal end 22 to be advanced through bodily passages. The drive shaft 40 may cooperate with a stabilizer position control 442 in the handle 410 in various implementations. For example, the driver knob 420 may be used as the stabilizer position control 442, so that pushing the driver knob 420 in the distal direction would position the drive shaft distal end 42 in the drive shaft second position 49 and pulling the driver knob 420 in the proximal direction would retract the drive shaft distal end 42 into the drive shaft first position 47 and correspondingly position the fixation structure 30 between the first fixation structure position 137 and the second fixation structure position 139.

The fixation structure 30 illustratively includes a helix 31, the interior annular surface of which defines an internal passage 35 about axis 39. The fixation structure 30 including the helix 31 may be made of any suitable material, including metals such as a platinum iridium alloy. The fixation structure proximal end 38 may be secured to the drive shaft distal end 42 in any desired manner. A distal portion of the fixation structure 30 illustratively defines a fixation structure tip 32. The fixation structure tip 32 may be sharpened and/or otherwise configured to penetrate the tissue 520 as the fixation structure 30 is rotated in order to draw the fixation structure 30 into the tissue 520. Counterclockwise rotation of the fixation structure 30 draws the fixation structure 30 into the tissue 520, and a clockwise rotation would release the fixation structure 30 from the tissue 520. In other implementations, the helix 31 may be reversed, so that a clockwise rotation draws the fixation structure 30 into the tissue 520 and a counterclockwise rotation releases the fixations structure 30 from the tissue 520.

Figure 2D:
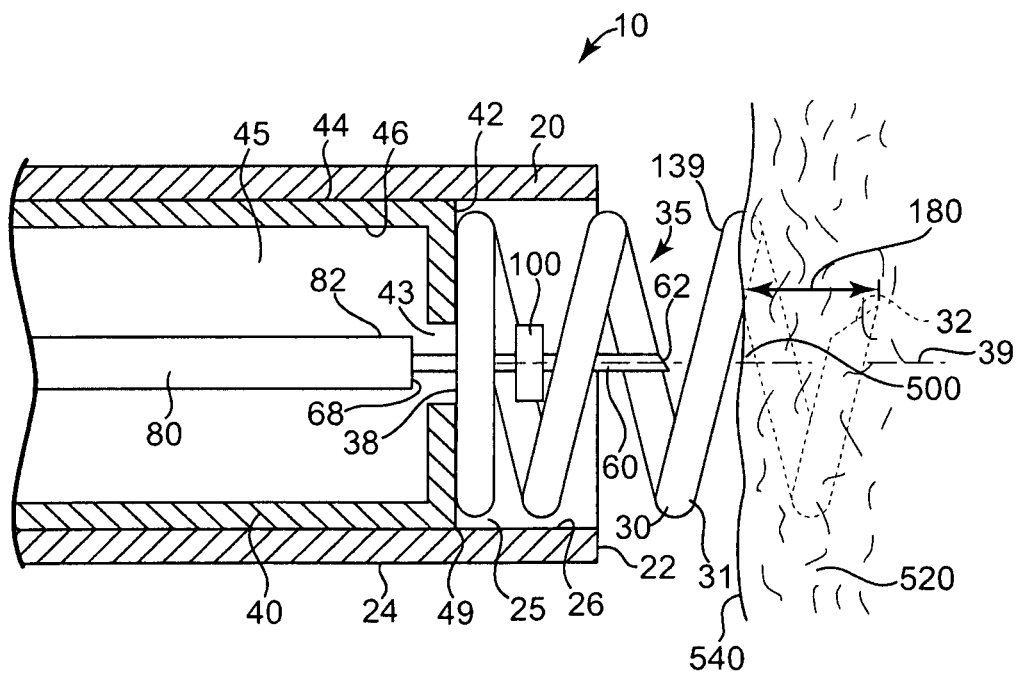
FIG. 2D is a partial cross-section view of a distal portion of an exemplary implementation of the injector apparatus of FIG. 1 in a in a fourth operational position.
Figure 2E:
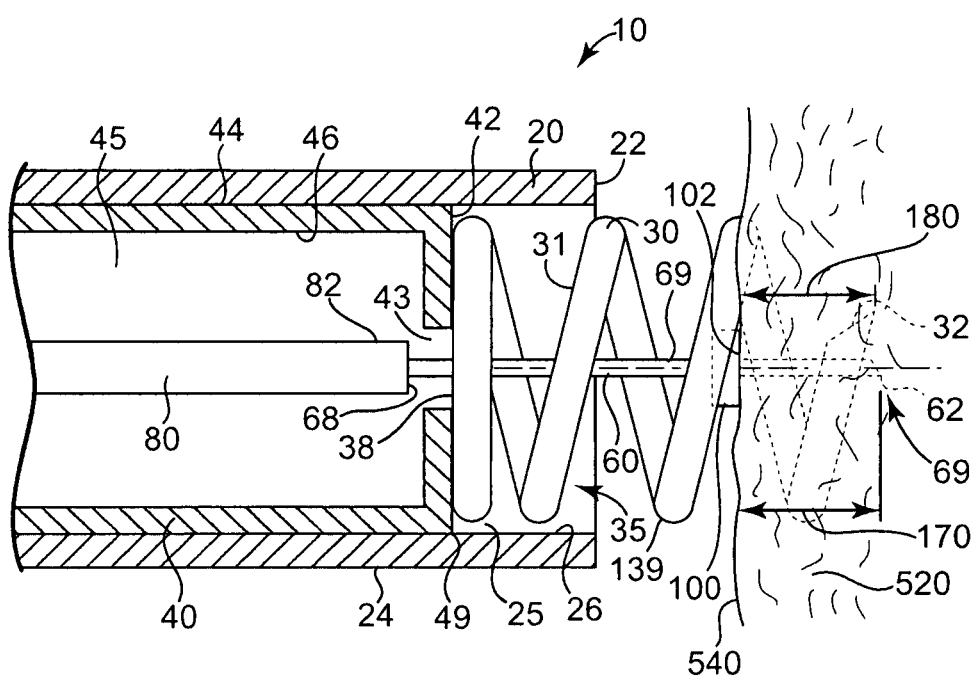
FIG. 2E is a partial cross-section view of a distal portion of an exemplary implementation of the injector apparatus of FIG. 1 in a in a fifth operational position.

As further illustrated in FIG. 2A, the injector apparatus 10 includes an injector needle 60 that has an injector needle tip 62 and an injector needle proximal end 68. The position of the injector needle 60 relative to the catheter body distal end 22 may be varied between at least a first injector needle position 67 and a second injector needle position 69 (FIG. 2E). The position of the injector needle 60 relative to the fixation structure 30 is varied as the injector needle 60 is alternated between the first injector needle position 67 and the second injector needle position 69. For example, the injector needle tip 62 may be well proximal of the fixation structure tip 32 with the injector needle 60 in the first injector needle position 67, and near to the fixation structure tip 32 (even with or proximal of or distal of) with the injector needle 60 in the second injector needle position 69.

In the first injector needle position 67, the injector needle 60 may reside within the catheter body lumen 25, as illustrated in FIG. 2A, with the injector needle tip 62 generally within the catheter body lumen 25 proximal of the catheter body distal end 22 and proximal of the fixation structure tip 32. The injector needle 60 in the first injector needle position 67 may be generally proximate the catheter body distal end 22 as illustrated in FIG. 2A, wherein the injector needle 60 in the first injector needle position 67 is located within the drive shaft lumen 45. In other implementations, at least a portion of the injector needle 60 may reside within internal passage 35 of the fixation structure 30.

The injector needle 60 may cooperate with an injector needle position control 444 in the handle 410 in various implementations. For example, the injector needle position control 444 (FIG. 1) may be configured as a sliding button 446 on the handle 410 that slides generally in a proximal-distal orientation along the handle 410. Sliding the sliding button 446 in the distal direction positions the injector needle 60 in the injector needle second position 69, while sliding the sliding button 446 in the proximal direction retracts the injector needle 60 into the injector needle first position 67. The injector needle 60 has an injector needle lumen 65 (FIG. 3A) in communication between an injector needle proximal end 68 and the injector needle tip 62 to communicate injectate from the injector needle proximal end 68 to the injector needle tip 62 for injection into tissue 520. The injector needle 60 may be made, for example, of steel or other metals or metal alloys.

FIG. 2B illustrates the drive shaft distal end 42 in the second position 49. The fixation structure 30 is correspondingly positioned in the second fixation structure position 139, in which at least a portion of the fixation structure 30 emerges from the catheter body lumen 25. As shown in FIG. 2C, the fixation structure 30 rotatably emerges from the catheter body lumen 25 so that the fixation structure tip 32 may penetrate tissue 520 proximate the injection site 500. The fixation structure tip 32 may be biased against the tissue 520 and the drive shaft 40 rotated to rotate the fixation structure 30 and screw the fixation structure 30 into the tissue 520 to the fixation depth 180 (FIG. 2D). In other implementations, the fixation structure 30 may be alternated between the first fixation structure position 137 and the second fixation structure position 139 in other ways, as would be recognized by one of ordinary skill in the art upon study of this disclosure. In still other implementations, the fixation structure 30 may be generally fixed in the second fixation structure position 139. Various implementations may omit the drive shaft 40, and the fixation structure 30 may be rotated by, for example, rotation of the catheter body 20 to draw the fixation structure 30 into the tissue 520 to the fixation depth 180. The fixation structure 30 may be rotated in other ways in order to penetrate into the tissue 520 to the fixation depth 180, as would be recognized by one of ordinary skill in the art upon study of this disclosure.

At least a portion of the fixation structure 30 penetrates into the tissue 520 to the fixation depth 180 sufficient to anchor the injector apparatus 10 to the tissue 520 proximate the injection site 500. The fixation structure 30 may penetrate into the tissue 520 until the catheter body distal end 22 is drawn into and biased against the tissue 520, or as shown in FIGS. 2C-2E, the fixation structure 30 may penetrate into the tissue 520 to a lesser degree such that the catheter body distal end 22 remains spaced away from the tissue 520. In either case, the catheter body distal end 22 is fixed with respect to the tissue 520.

As illustrated in FIG. 2D, an injector needle 60 lies generally along the axis 39, and includes a stop 100 for limiting the penetration of the injector needle into the tissue 520. The stop 100 is illustrated as a disc of a size capable of passing through aperture 43 and through internal passage 35, although a variety of other shapes and sizes are suitable for the stop 100. With the fixation structure 30 fixed within the tissue 520 proximate the injection site 500 at the fixation depth 180 to anchor the catheter body proximal end 22 of the catheter body 20, the injector needle 60 is advanced distally from the injector needle first position 67 to protrude through the aperture 43 and into the internal passage 35 defined by the helix 31 of fixation structure 30. The injector needle 60 moves relative to the fixation structure 30 as the injector needle is advanced from the injector needle first position 67. The injector needle 60 is advanced relative to the catheter body distal end 22 and relative to the fixation structure 30 to the second injector needle position 69 (FIG. 2E) wherein the injector needle penetrates the myocardium until the stop engages the epicardium/endocardium.

FIG. 2E illustrates the injector needle 60 positioned in the second injector needle position 69 to penetrate into the tissue 520 to a penetration depth 170 regulated by the position of the stop 100 with respect to the injector needle tip 62. The distal face 102 of the stop 100 is biased against the epicardium/endocardium 540 to regulate the penetration depth 170 of the injector needle 60. The catheter body distal end 22 is fixed with respect to the tissue 520 (in a spaced away position as shown). The penetration depth 170 of the injector needle 60 may be equal to, less than, or greater than the fixation depth 180 of the fixation structure 30. As illustrated, the injector needle tip 62 is generally at the same depth as the fixation structure tip 32, but in other implementations may be distal of the fixation structure tip 32 or proximal of the fixation structure tip 32, as desired. The penetration depth 170 to which the injector needle 60 penetrates the tissue 520 is determined by the position of the stop 100 with respect to the injector needle tip 62, and is independent of the fixation depth 180 to which the fixation structure 30 penetrates the tissue 520.

In the implementation of FIGS. 2A-2E, the injector needle 60 is in fluid communication with an injector catheter 80. When the injector needle 60 is fully deployed, the distal end of the injector catheter 80 and the injector needle proximal end 68 are proximal of the drive shaft distal end 42 and proximal of the aperture 43. In other implementations, the injector catheter 80 may extend through the aperture 43 such that the injector catheter distal end 82 may lie generally within the internal passage 35, and the injector needle proximal end 68 may be distal of the aperture 43 and may lie generally within the internal passage 35 of the helix 31.

In the implementation of FIGS. 2A-2E, before deployment, the injector needle 60 and the stop 100 are recessed behind the aperture 43. Alternatively, the injector needle 60 may extend into the internal passage 35 behind the catheter body distal end 22. In such an alternative implementation, the stop 100 may reside either behind or in front of the aperture 43. If the stop 100 need not pass through the aperture 43 during deployment of the injector needle 60, it may be larger than the aperture 43 provided it may still pass through the internal passage 35 of the helix 31.

Although the stabilizer used in the illustrative implementation of FIGS. 2A-2E is a fixation structure, and more particularly, a fixation structure that includes portions configured as a helix 31 designed to penetrate tissue 520 generally proximate the injection site 500 by being screwed into the tissue 520, other types of fixation structures and more generally, other types of stabilizers may be used. A mechanical claw or a suction pad are alternatives.

Figure 3A:
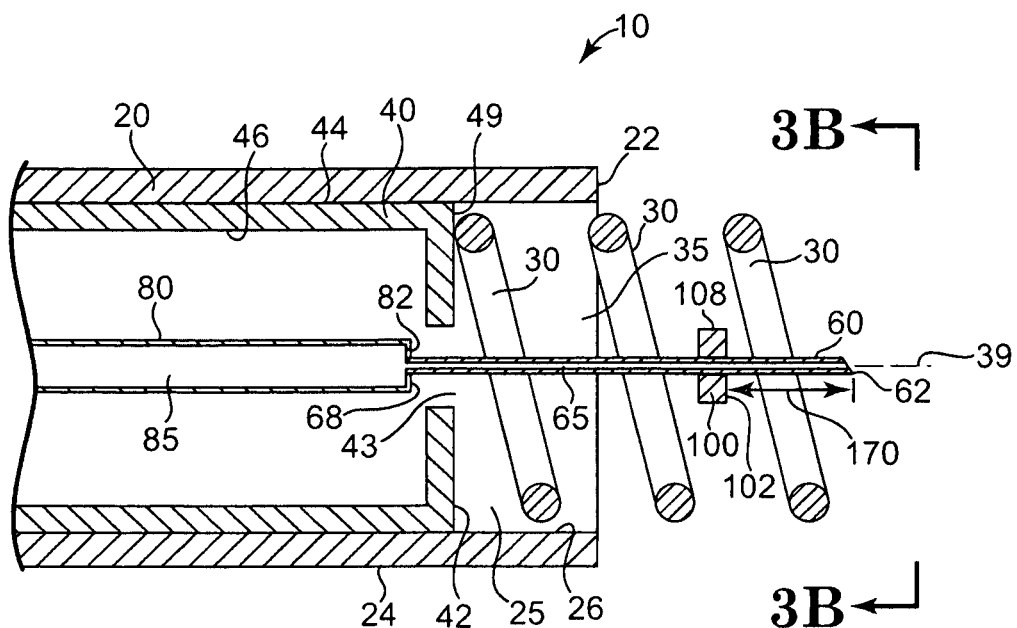
FIG. 3A is a longitudinal cross-section view of a distal portion of the exemplary implementation of the injector apparatus of FIG. 1.
Figure 3B:
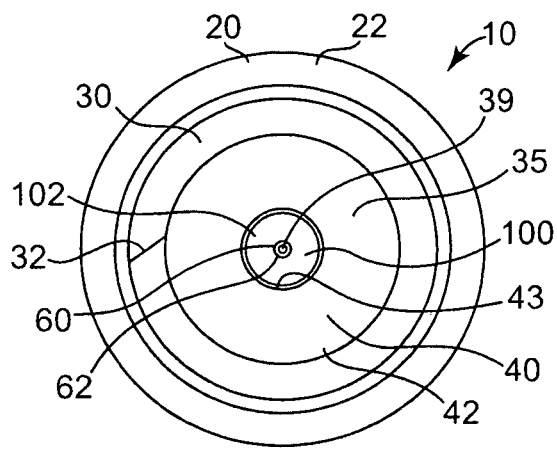
FIG. 3B is a plan view from plane 3A-3A of the distal portion of the exemplary implementation of the injector apparatus of FIG. 3A.

A cut-away view of an illustrative implementation of the injector apparatus 10 is illustrated in FIG. 3A and a transverse plan view is illustrated in FIG. 3B. As illustrated in FIG. 3A, the proximal end 68 of the injector needle 60 is secured to the distal end 82 of the injector catheter 80 so that the injector needle lumen 65 is in communication with the injector catheter lumen 85. The injector needle 60 is generally aligned with axis 39. Stop 100 is illustrated as having a disc-shaped configuration sized to pass through the internal passage 35 defined by the fixation structure 30.

As shown in greater detail in FIG. 3A, an injector catheter 80 defines an injector catheter lumen 85, an injector catheter distal end 82, and an injector catheter proximal end (not shown). The injector catheter distal end 82 is secured to the injector needle proximal end 68 to communicate injectate into the injector needle lumen 65. The injector catheter lumen 85 generally at the injector catheter proximal end (see FIG. 1) may communicate with port 430 on the handle 410 so that injectate may be communicated through port 430 into the injector catheter lumen 85, and thence through the injector needle lumen 65 into the tissue 520 at the injection site 500. In other implementations, a reservoir (not shown) may be located within the catheter body lumen 25 in communication with the injector catheter lumen 85 to communicate injectate into the injector catheter lumen 85, and thence into the injector needle lumen 65, and the injectate may be delivered upon receipt of a signal communicated from the handle 410 to the reservoir. In still another implementation, the injector needle proximal end 68 may be located near the reservoir so that the reservoir may communicate substantially directly with the injector lumen 65. Where the injectate is a multiple component injectate, the injector catheter lumen 85 may be a dual lumen (two lumen arranged side-by-side or coaxially) which communicate with respective ports on the handle 410. The components may mix before passing into the injector catheter lumen 85, or may pass into respective lumen within the injector needle 60 and mix within the tissue 520 after injection therein.

As further shown in FIG. 3A, the stop 100 extends circumferentially about a portion of the injector needle 60 to limit the penetration of the injector needle 60 into the tissue 520. In the illustrative implementation of FIG. 3A, the stop 100 has a distal face 102 and a proximal face 108. The stop 100 is sized to pass through the aperture 43 and internal passage 35.

As shown in FIG. 3B, the injector needle 60 and the stop 100 pass through the aperture 43 defined by the drive shaft distal end 42 of the drive shaft 40, and through the internal passage 35 defined by the helix 31 and generally along the axis 39. With the injector needle 60 in the injector needle second position 69, the distal face 102 of the stop 100 is biased against the epicardium/endocardium 540 to establish the penetration depth 170 and to prevent further penetration of the injector needle 60 into the myocardial tissue 520.

The stop 100 may be secured in any desired manner to the injector needle 60 at a specific location with respect to the injector needle tip 62, and the location may be fixed or variable. Fixation may be achieved in any desired manner, such as, for example, by welding or gluing. Moreover, the stop 100 may be implemented by a thickened region of the injector needle itself. In implementations having a variably positionable stop, the stop may be secured to the injector needle 60 by, for example, a set screw or set nut (not shown) to allow adjustment of the location of the stop with respect to the injector needle tip 62.

FIG. 3B illustrates the injector needle 60 generally aligned with axis 39 to allow the stop 100 to pass through the aperture 43 and through the internal passage 35. The stop 100, as illustrated, is sized to pass through the internal passage 35.

Although shown as a catheter in FIGS. 2A-2E and FIGS. 3A-3B, the injector catheter lumen 85 may be implemented in other ways. An illustrative alternative implementation is as a bore through a core of the catheter body, with a deployment mechanism for the injector needle 60 being provided within the drive shaft distal end 42.

Figure 4:
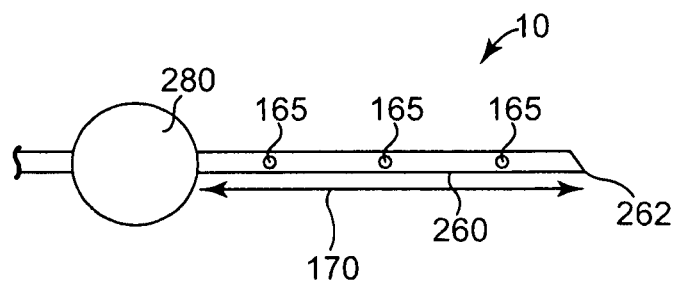
FIG. 4 is a side plan view of a portion of an alternative implementation of an injector needle and stop.

The stop 100 may be made in a variety of different shapes, including, for example, generally disc-shaped, generally spherical, generally ellipsoidal, generally oblate spheroidal, or any other shape that is suitable for passing through the internal passage 35 without being entrapped by the helix 31, and that is effective for limiting the penetration of the injector needle 60 into the tissue 520. FIG. 4 shows an alternative illustrative implementation of an injector needle 260 that includes a stop 280 and injection ports 165. The injection ports 165 are located along the injector needle 260 between the injector needle tip 262 and the stop 280. Injectate may be introduced into the tissue 520 through the injection ports 165 as well as through the injector needle tip 262 in order to disperse injectate into the tissue 520 generally throughout the penetration depth 170. The stop 280, as illustrated, has a generally spherical shape, to facilitate passage of the stop 280 through the internal passage 35 without being caught on portions of the helix 31.

An illustrative method of administering an injection into the myocardial tissue 520 through the epicardium using the injector apparatus 10 is as follows. The catheter body 10 is inserted into the thoracic cavity with the fixation structure 30 in a first fixation structure position 137 contained within the catheter body lumen 25. The catheter body distal end 22 is navigated through the thoracic cavity and through an opening in the pericardial sac until generally proximate the injection site 500 on the epicardium 540. When the catheter body distal end 22 is positioned proximate the epicardium 540, the fixation structure 30 is deployed from the first fixation structure position 137 to the second fixation structure position 139. This may be accomplished by positioning the drive shaft 40 from the first drive shaft position 47 to the second drive shaft position 49. The fixation structure tip 32 is brought into engagement with the epicardium 540, and then the fixation structure 30 is rotated so that the fixation structure 30 penetrates into the tissue 520. The fixation structure proximal end 38 of the fixation structure 30 is engaged with the drive shaft 40 so that the fixation structure 30 is rotated by rotation of the drive shaft 40. The fixation structure 30 is rotated until the fixation structure penetrates into the tissue 520 in an amount sufficient to secure the catheter body distal end 22 to the tissue 520. Then, the injector needle 60 is advanced from the first injector needle position 67 to the second injector needle position 69, so that the injector needle 60 penetrates the tissue 520 to the penetration depth 710 from the injector needle tip 62 to the stop 100. The injectate is then delivered into the tissue 520 through the injector needle 60.

After delivery of the injectate, the injector needle 60 is retracted to the first injector needle position 67 in order to withdraw the injector needle 60 from the tissue 520. The fixation structure 30 is then rotated to withdraw the fixation structure 30 from the tissue 520, and the fixation structure 30 is then retracted from the second fixation structure position 139 to the first fixation structure position 137. The catheter body 20 is then withdrawn from the thoracic cavity. Alternatively, the catheter body distal end 22 may be redeployed generally proximate another injection site 500 along the epicardium 540 to deliver an injection of injectate at that injection site 500. As part of redeploying the catheter body distal end 22 at one or more additional injection sites 500, these operations or combinations or subcombinations thereof may be repeated. Repeatedly redeploying the catheter over a number of injection sites 500 delivers a number of injections of injectate at a number of injection sites 500 along the epicardium 540.

Various controls may be arranged about the handle 410 and/or other portions of the injector apparatus 10 to aid the physician in directing the catheter body distal end 22 to the epicardium/endocardium 540, to position the fixation structure 30 between the first fixation structure position 137 and the second fixation structure position 139, to position the injector needle between the first injector needle position 167 and the second injector needle position 169, and to cause the injectate to be delivered to the tissue 520 through the injector needle 60. Suitable controls would be known to one of ordinary skill in the art upon study of this disclosure.

The various exemplary implementations described herein are illustrative of the invention. Variations and modifications of these implementations are possible, and practical alternatives to and equivalents of the various elements of the embodiments are contemplated. These and other variations and modifications of the implementations disclosed herein may be made without departing from the scope and spirit of the invention, as set forth in the following claims.

What is claimed is:

1. An apparatus for administering an injectate into myocardial tissue of a heart of a patient, comprising: a body having a distal portion; a stabilizer disposed at the body distal portion for stabilizing the body distal portion relative to the myocardial tissue; a needle controllably extendable distally from the body distal portion, the needle comprising a needle tip and an enlarged region disposed along the needle a predetermined distance from the needle tip for engaging the myocardial tissue during distal extension to limit penetration of the needle into the myocardial tissue to a predetermined penetration depth, and further comprising an injection port distal of the enlarged region; and a lumen for receiving the injectate, the lumen being in fluid communication with the injection port through the needle for conveying the injectate to the injection port; wherein the stabilizer comprises a helix adapted to be screwed into the myocardial tissue to a fixation depth, the penetration depth of the needle being equal to and independent of the fixation depth of the helix.

2. The apparatus of claim 1 further comprising a control mechanism for controllably retaining the needle tip in an atraumatic retracted position within the body distal portion, and extending the needle tip distally from the body distal portion.

3. The apparatus of claim 1 wherein the enlarged region is adjustably disposed with respect to the needle tip along the needle for setting the predetermined distance from the needle tip.

4. The apparatus of claim 1 wherein the body is a catheter body and the distal portion is a distal end of the catheter body.

5. The apparatus of claim 4, further comprising: a handle secured to a proximal end of the catheter body; a driver knob mounted on the handle; and a drive shaft extending through the catheter body and having a proximal end coupled to the driver knob and a distal end coupled to the helix for controllably rotating the helix upon manipulation of the driver knob between an atraumatic retracted position within the body distal portion and an extended portion.

6. The apparatus of claim 5 further comprising:
a slider mounted on the handle; and
an injector catheter having a proximal end coupled to the slider and a distal end coupled to the needle for controllably positioning the needle tip between an atraumatic retracted position within the body distal portion and an extended position.

7. The apparatus of claim 1 wherein the body is a handheld unit and the distal portion is a projecting surface of the handheld unit.

8. The apparatus of claim 1 wherein the injection port is disposed at the needle tip.

9. The apparatus of claim 1 wherein the injection port is disposed in a sidewall of the needle.

10. The apparatus of claim 1 wherein the injection port is disposed at the needle tip, further comprising a plurality of additional injection ports disposed along a sidewall of the needle distal of the enlarged region.

11. The apparatus of claim 1 wherein:
the injectate comprises a first injectable component and a second injectable component; and
the lumen comprises a first lumen member for receiving the first injectable component, and a second lumen member for receiving the second injectable component;
the injection port being in fluid communication with the first lumen member and the second lumen member.

12. The apparatus of claim 1 further comprising:
an additional injection port distal of the enlarged region;
wherein the injectate comprises a first injectable component and a second injectable component;
wherein the lumen comprises a first lumen member for receiving the first injectable component, and a second lumen member for receiving the second injectable component;
wherein the injection port is in fluid communication with the first lumen member; and
wherein the additional injection port is in fluid communication with the second lumen member.

13. An apparatus for administering an injectate into myocardial tissue of a heart of a patient, comprising: a body having a distal portion; a helical stabilizer disposed at the body distal portion and adapted to be screwed into the myocardial tissue for stabilizing the body distal portion relative to the myocardial tissue, the helical stabilizer having an interior annular surface defining an internal passage about an axis; a needle comprising a needle tip, an enlarged region disposed along the needle a predetermined distance from the needle tip, and an injection port distal of the enlarged region, the needle being controllably movable along the axis of the helical stabilizer between a proximal portion and a distal position, and the enlarged region having a distal face unimpeded by the helical stabilizer when disposed within the internal passage of the helical stabilizer; and a lumen in fluid communication with the injection port through the needle for conveying the injectate to the injection port; wherein the enlarged region establishes a predetermined penetration depth of the needle into the myocardial tissue essentially equal to the predetermined distance of the enlarged region from the needle tip; and wherein the helical stabilizer is adapted to be screwed into the myocardial tissue to a fixation depth, the predetermined penetration depth of the needle being equal to and independent of the fixation depth of the helical stabilizer.

14. The apparatus of claim 13 wherein the enlarged region is adjustably disposed with respect to the needle tip along the needle for setting the predetermined distance from the needle tip.

15. The apparatus of claim 13 wherein the body is a catheter body and the distal portion is a distal end of the catheter body.

16. The apparatus of claim 13 wherein the body is a handheld unit and the distal portion is a projecting surface of the handheld unit.

* * * * *